United States Patent [19]

Takamura et al.

[11] Patent Number: 4,745,471
[45] Date of Patent: May 17, 1988

[54] SOLID-STATE IMAGING APPARATUS AND ENDOSCOPE

[75] Inventors: Koji Takamura; Haruhiko Kaiya, both of Tokyo, Japan

[73] Assignee: Olympus Optical Co., Ltd., Tokyo, Japan

[21] Appl. No.: 49,720

[22] Filed: May 12, 1987

[30] Foreign Application Priority Data

| May 13, 1986 [JP] | Japan | 61-109081 |
| May 14, 1986 [JP] | Japan | 61-109753 |
| May 15, 1986 [JP] | Japan | 61-111133 |

[51] Int. Cl.$^4$ .......... H04N 7/18; A61B 1/06; A61B 1/04
[52] U.S. Cl. .......... 358/98; 128/6; 358/213.11
[58] Field of Search ........... 358/98, 213.11; 128/4, 128/6

[56] References Cited

U.S. PATENT DOCUMENTS

| 4,442,456 | 4/1984 | Iwata | 358/213.11 |
| 4,491,865 | 1/1985 | Danna | 358/98 |
| 4,573,450 | 3/1986 | Arakawa | 358/98 |
| 4,594,613 | 6/1986 | Shinbori | 358/213.11 |

FOREIGN PATENT DOCUMENTS

| 55-124366 | 3/1979 | Japan . |
| 60-62279 | 9/1983 | Japan . |
| 60-208726 | 4/1984 | Japan . |

Primary Examiner—Howard W. Britton

[57] ABSTRACT

An endoscope includes an operation section and an insertion section extending from the operation section. In a distal end portion of the insertion section is arranged a solid-state imaging apparatus 40 for converting an optical image imaged by an objective unit into an electric signal and outputting the signal. The imaging apparatus includes a base and a solid-state imaging element tip mounted on the base and having a light-receiving section and a plurality of electrodes. A plurality of leads are provided at the base. A transparent cover plate is fixed to the base and has a surface facing the light-receiving section. A lead pattern is formed on the surface of the cover plate and electrically connects the leads and the electrodes.

11 Claims, 5 Drawing Sheets

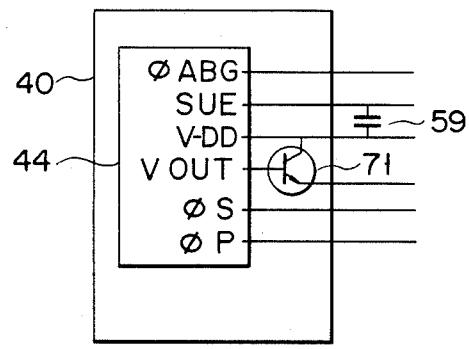
F I G. 7
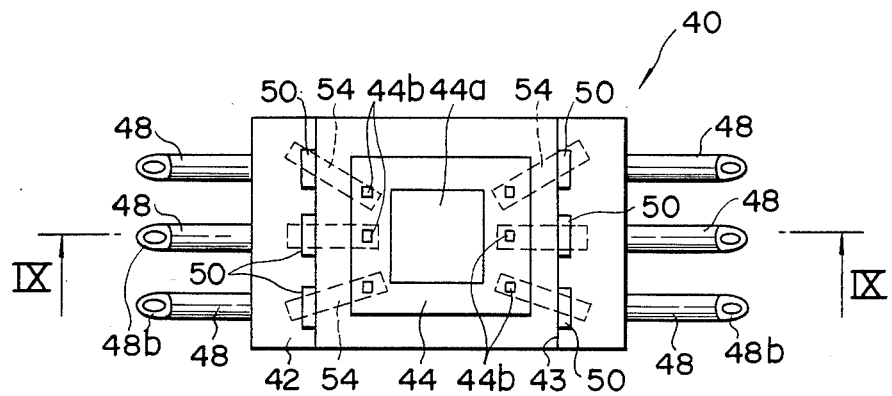
F I G. 8
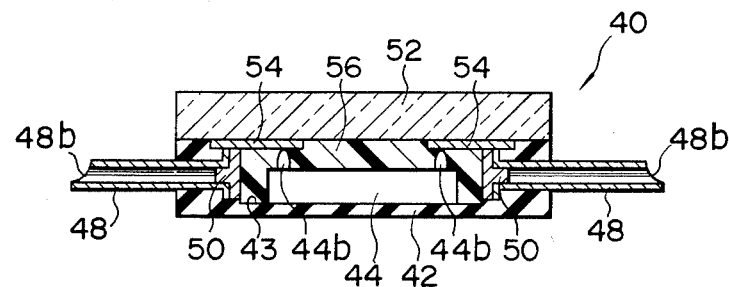
F I G. 9

4,745,471

SOLID-STATE IMAGING APPARATUS AND ENDOSCOPE

BACKGROUND OF THE INVENTION

The present invention relates to a solid-state imaging apparatus and an endoscope comprising the solid-state imaging apparatus.

In recent years, there has been proposed an endoscope which uses a solid-state imaging apparatus, as an imaging optical system, in place of an optical fiber. In general, a solid-state imaging apparatus of this type comprises a base made of a metal, ceramic, or the like, and an imaging element chip adhered to the base by a eutectic crystal alloy, low-melting point glass, or the like. A plurality of external lead terminals are mounted on the base, and these lead terminals are connected to Al-electrodes of the chip by means of thin metal wires (bonding wires). A glass plate cover is adhered onto the upper surface of the chip and the base to provide a seal to the chip.

However, in the solid-state imaging apparatus with the above arrangement, the electrodes of the chip are connected to the external lead terminals through the bonding wires. Therefore, the overall apparatus becomes bulky, and the connecting operation is cumbersome, resulting in poor productivity. The solid-state imaging apparatus is arranged in a distal end portion of an endoscope insertion section. If the imaging apparatus has a large size, the insertion section becomes bulky.

SUMMARY OF THE INVENTION

The present invention has been made in consideration of the above situation and has as its object to provide a compact solid-state imaging apparatus which can facilitate connecting operation, and an endoscope which uses the solid-state imaging apparatus and can allow its insertion section to be compact.

In order to achieve the above object, a solid-state imaging apparatus according to the present invention comprises: a base; a solid-state imaging element chip provided at the base and having a light-receiving section and a plurality of electrodes; a plurality of leads provided at the base; and a transparent cover fixed on the base, the cover having a surface facing the light-receiving section of the chip and a lead pattern which is formed on the surface and electrically connects the electrodes of the chip and the leads.

The endoscope according to the present invention is constructed using the solid-state imaging apparatus having the above arrangement.

BRIEF DESCRIPTION OF THE DRAWINGS

FIGS. 1 to 7 show an endoscope according to an embodiment of the present invention, in which FIG. 1 is a schematic view showing the overall endoscope, FIG. 2 is a sectional view of a distal end portion of an insertion section of the endoscope, FIG. 3 is a plan view of a solid-state imaging apparatus, FIG. 4 is a sectional view taken along a line IV—IV in FIG. 3, FIG. 5 is a rear view of the imaging apparatus, FIG. 6 is a sectional view showing a connecting portion of a lead terminal, and FIG. 7 is a view schematically showing an electrical circuit of the imaging apparatus;

FIGS. 8 and 9 show a modification of the solid-state imaging apparatus, in which FIG. 8 is a plan view thereof and FIG. 9 is a sectional view taken along a line IX—IX in FIG. 8; and FIGS. 10 to 13 show an endoscope according to a second embodiment of the present invention, in which FIG. 10 is a sectional view of a distal end section of an insertion section of the endoscope, FIG. 11 is a plan view of a solid-state imaging apparatus, FIG. 12 is a sectional view taken along a line XII—XII in FIG. 11, and FIG. 13 is a perspective view showing a coupling member.

DETAILED DESCRIPTION OF THE PREFERRED EMBODIMENTS

Embodiments of the present invention will now be described with reference to the accompanying drawings.

Figure 1:
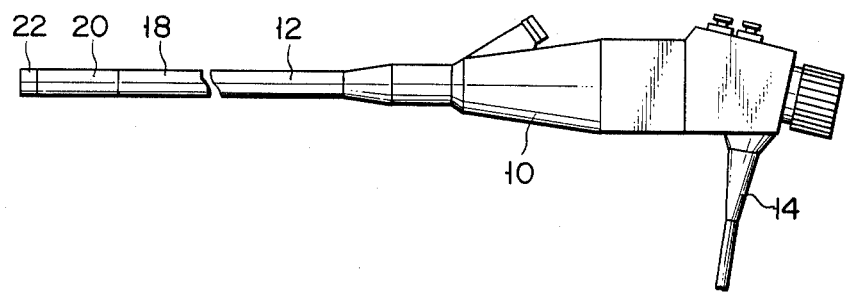

FIG. 1 shows the overall endoscope. As is shown in FIG. 1, the endoscope comprises operation section 10, insertion section 12 extending from the operation section, and universal cord 14 extending from the operation section. Insertion section 12 has flexible sheath 18, bendable portion 20 provided at the distal end portion of the sheath, and distal end member 22 fixed to the distal end of the bendable portion.

Figure 2:
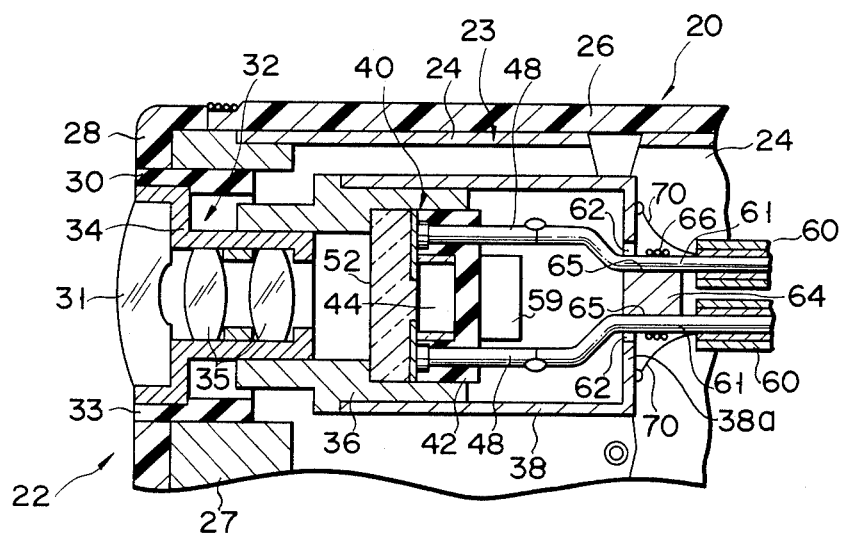

As shown in FIG. 2, bendable portion 20 includes core assembly 23 having a plurality of ring members 24 rotatably coupled to each other, and outer tube 26 covering on the outer surface of the core assembly. The outer tube is formed of a synthetic resin having electrically insulating properties. Distal end member 22 has body 27 fixed to the distal end of core assembly 23 and cover 28 which covers the outer surface of the body and has electrically insulating properties. In end member 20 are formed mounting hole 30 for receiving an observation optical system, a mounting hole for an illumination optical system (not shown), a channel hole, and the like.

Objective unit 32 is arranged in mounting hole 30. Unit 32 has lens frame 34 fitted in mounting hole 30 through electrically insulating cylinder 33 and a plurality of objective lenses 35 coaxially arranged in the lens frame. Observation window 31 is mounted on the front end of lens frame 34. A distal end of cylindrical element frame 36 is fitted in the rear end of lens frame 34, and frame 36 extends coaxially with lens frame 34. Cylindrical shielding frame 38 is fitted in the rear end of element frame 36, and extends coaxially with the element frame. The rear end of shielding frame 38 is closed by rear wall 38a.

Figure 3:
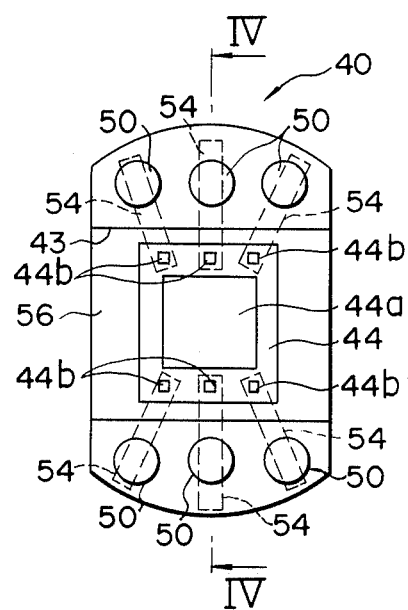
Figure 4:
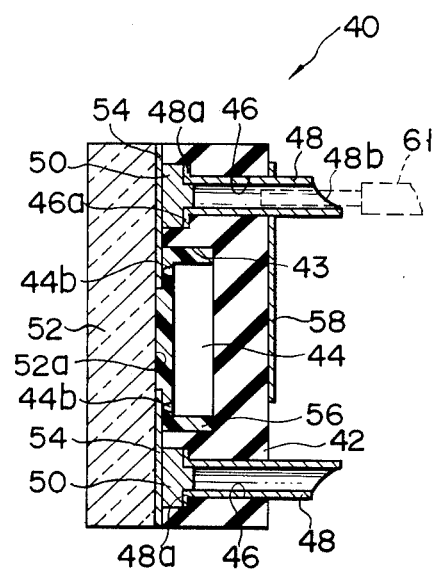

Solid-state imaging apparatus 40 is arranged in element frame 36 to face objective unit 32. As is shown in FIGS. 2 to 4, imaging apparatus 40 comprises rectangular base 42 formed of an electrically insulating material such as ceramic. Recess 43 is formed in the front surface of base 42, and solid-state imaging element chip 44 is received in the recess and adhered to the bottom thereof. Light-receiving surface 44a is formed on the upper surface of chip 44, and three electrodes 44b are formed at each side of the light-receiving surface by aluminum deposition. Three mounting holes 46 are cut in each of the opposing end portions of base 42. The recess 43 is located at the center of base 42. Each mounting hole 46 extends in a direction perpendicular to the front surface of base 42, and has stepped portion 46a. Cylindrical external lead 48 is inserted in mounting hole 46, and partially extends from the rear surface of base 42. Each external lead 48 has flange 48a at its front end, and the flange is adhered to stepped portion 46a of corresponding mounting hole 46. Metal electrode lid 50 is fitted in the end of each mounting hole 46 open to the front surface of base 42 to close the opened end. Lid 50 is engaged with flange 48a of external lead 48. The extended end of external lead 48 is obliquely cut, and cut surface 48b is directed to the outside of base 42.

Figure 5:
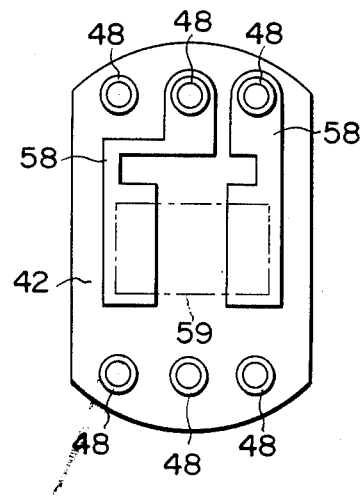

A transparent cover plate, e.g., glass plate 52 having the same shape as that of base 42 is adhered to the front surface of base 42. Lead pattern 54 is formed on rear surface 52a of plate 52, i.e., a surface on the side of base 42. Lead pattern 54 is face-bonded to electrodes 44b of chip 44 and electrode lids 50. Thus, electrodes 44b are electrically connected to corresponding leads 48 by means of lead pattern 54. Transparent electrically insulating resin 56 is filled in a space between base 42 and glass plate 52 and around chip 44, thereby providing a seal to chip 44. As is shown in FIGS. 4 and 5, second lead pattern 58 is formed on the rear surface of base 42 by photoetching. Lead pattern 58 is bonded to leads 48 by soldering and is electrically connected thereto. An electrical par! for solid-state imaging apparatus 40, e.g., capacitor 59, is mounted on the rear surface of base 42 and is electrically connected to lead pattern 58.

Figure 6:
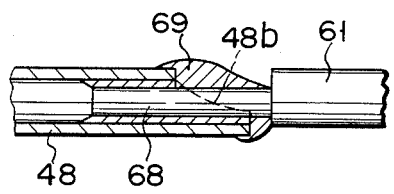

As is shown in FIG. 2, solid-state imaging apparatus 40 is mounted in element frame 36 so that glass plate 52 faces objective unit 32. An optical image incident on the endoscope through observation window 31 is focused on light-receiving surface 44a of element chip 44 by objective lenses 35. Solid-state imaging apparatus 40 converts the optical image focused on light-receiving surface 44a into an electrical signal and outputs the signal. A plurality of coaxial cables 60 are connected to imaging apparatus 40. Cables 60 extend through insertion section 12 of the endoscope, and distal end portions of signal lines 61 of cables 60 are inserted in shielding frame 38 through a plurality of through holes 62 formed in rear wall 38a of frame 38. Fixing member 64 projects from rear wall 38a of frame 38, and a plurality of grooves 65 are formed on the outer surface of the fixing member. Signal lines 61 are fitted in grooves 65 of fixing member 64 and are fastened to the fixing member by wire 66. As is shown in FIGS. 2 and 6, core wire 68 projecting from the distal end of signal line 61 is inserted in corresponding external lead 48 of imaging apparatus 40, and is brazed thereto by soldering 69. Shield line 70 of each coaxial cable 60 is bonded to rear wall 38a of frame 38 by soldering.

FIG. 7 schematically shows an electrical circuit of solid-state imaging apparatus 40. Transistor 71 is arranged on an internal circuit of element chip 44, and capacitor 59 is externally connected.

According to solid-state imaging apparatus 40 of the endoscope with the above arrangement, external leads 48 and electrodes 44b of element chip 44 can be electrically connected to each other through lead pattern 54 formed on rear surface 52a of glass plate 52 without using bonding wires. For this reason, a space for the bonding wires is not required in front of base 42, so that imaging apparatus 40 can be rendered compact. In particular, dimensions in a direction perpendicular to light-receiving surface 44a of element chip 44 can be reduced. Since electrodes 44b and external leads 48 can be face-bonded to lead pattern 54, troubles such as open- or short-circuiting of the lead pattern can be eliminated and connections of electrodes 44b can be facilitated. Furthermore, since glass plate 52 is transparent, electrodes 44b of chip 44 can be observed from the side of the glass plate. Therefore, alignment between lead pattern 54 and electrodes 44b of the chip can be facilitated without using a special-purpose device.

Each external lead 48 has a hollow structure, and each line 61 can be directly connected to the external lead by inserting its core wire 68 into the external lead. For this reason, a terminal, a base, and the like for connecting the external leads and signal lines are not necessary. Therefore, the number of components can be reduced, the connecting operation can become easy, and the overall apparatus can be made compact. Since the distal end of external lead 48 is obliquely cut, the core line of the signal line can be easily inserted therein and soldering can also be facilitated.

Second lead pattern 58 is formed on the rear surface of base 42, and electrical parts accompanied with imaging apparatus 40 are mounted thereon. For this reason, a special-purpose base for mounting electrical parts need not be used, and a decrease in the number of components and a reduction in size of the imaging apparatus can be further promoted.

Since solid-state imaging apparatus 40 can be rendered compact as described above, the diameter of the distal end portion of the insertion section of the endoscope can be reduced and its axial length can be shortened. Therefore, the performance of the endoscope can be improved.

In the above embodiment, a so-called direct-observation type endoscope having an observation window at the distal end face of the insertion section is exemplified. However, the present invention is not limited to this, but can be applied to a side-observation type endoscope having an observation window at an outer periphery of the distal end portion of the insertion section. When the present invention is applied to the side-observation type endoscope, external leads 48 of solid-state imaging apparatus 40 can be arranged to extend from base 42 in a direction parallel to light-receiving surface 44a of element chip 44, as is shown in FIGS. 8 and 9. Note that the same reference numerals in FIGS. 8 and 9 denote the same parts as in the above embodiment, and a detailed description thereof will be omitted.

FIGS. 10 to 13 show an endoscope according to a second embodiment of the present invention. In these figures, the same reference numerals are used to designate the same parts as used in the first embodiment, and a detailed description of the same parts will be omitted.

Figure 10:
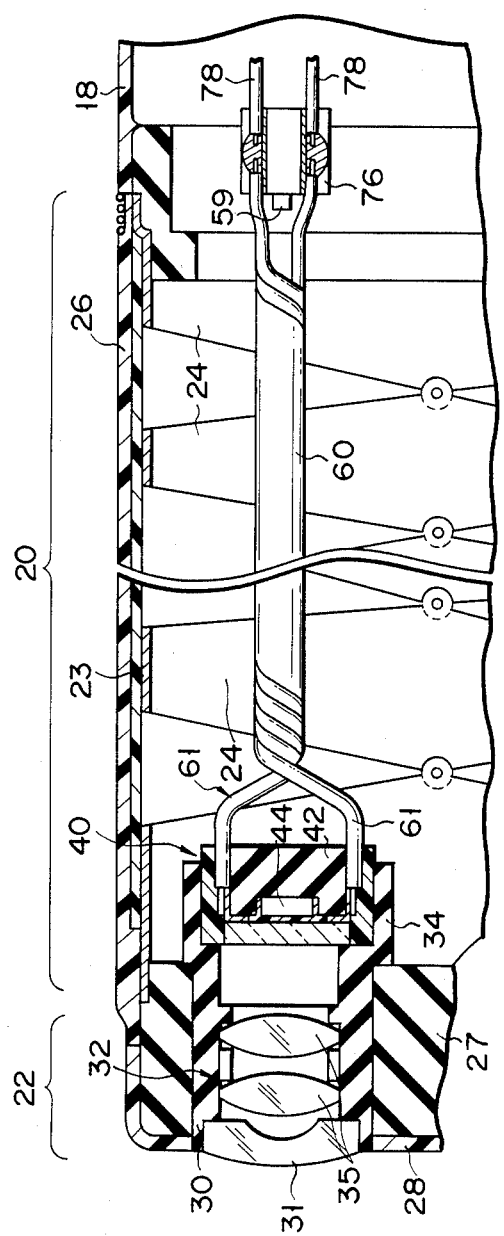
Figure 11:
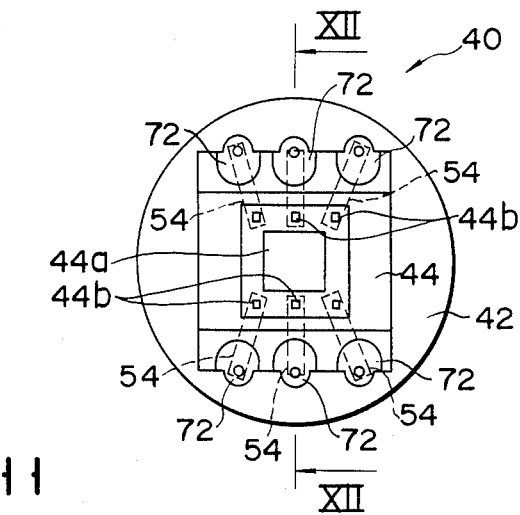
Figure 12:
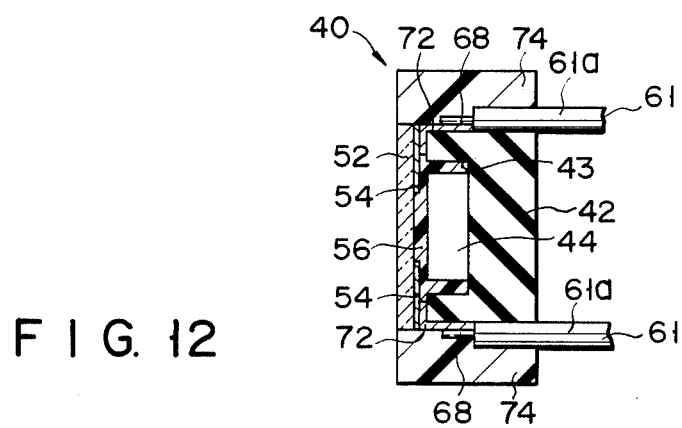
Figure 13:
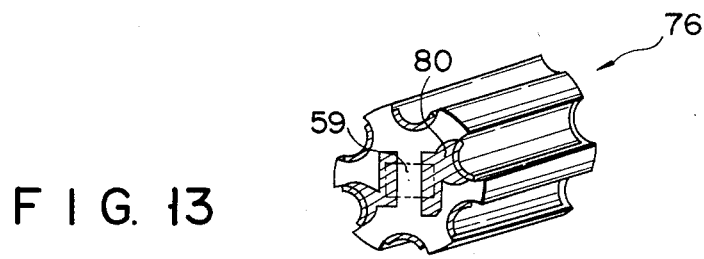

As is shown in FIG. 10, solid-state imaging apparatus 40 is mounted on the rear end of lens frame 34 and faces objective lenses 35. As is shown in FIG. 11 and 12, solid-state imaging element chip 44 is fixed in recess 43 of base 42. Three L-shaped leads 72 are fixed to each of the opposing end portions of base 42. Each lead 72 extends from the front surface to the side surface of base 42. Glass plate 52, on the rear surface of which lead pattern 54 is formed, is fixed to the front surface of base 42. Leads 72 are electrically connected to corresponding electrodes 44b of chip 44 by lead pattern 54. Transparent resin 56 having electrically insulating properties is filled in a space around chip 44.

In the second embodiment, imaging apparatus 40 comprises no external leads, and signal lines 61 are directly connected to leads 72. More specifically, core wire 68 of signal line 61 is adhered to that portion of corresponding lead 72 which is located on the side surface of base 42. The distal end portion of the signal line including insulating coat 61a, leads 72, and side surface of base 42 are sealed by transparent resin 74.

Each signal line 61 has a length larger than that of bendable portion 20 of insertion section 12, e.g., 50 mm or longer, and extends from imaging apparatus 40 beyond the rear end of the bendable portion. Referring to FIGS. 10 to 13, signal lines 61 are connected to coupling member 76 arranged at a connecting portion between bendable portion 20 and sheath 18. Coupling member 76 is connected to signal lines 78 extending from the side of operation section 10. Thus, signal lines 61 and 78 are connected to each other through coupling member 76. Lead pattern 80 is formed on the coupling member. An electrical part for imaging apparatus 40, e.g., capacitor 59, is fixed to coupling member 76 and is electrically connected to lead pattern 80.

According to the second embodiment with the above structure, since leads 72 of imaging apparatus 40 and electrodes 44b of chip 44 are connected to each other by lead pattern 54 formed on glass plate 52, bonding wires and a mounting space therefor can be omitted. Therefore, imaging apparatus 40 can be rendered compact and the connecting operation can be facilitated. Since signal lines 61 are connected to leads 72, connecting terminals and a base can be omitted. For the distal end portion of each signal line 61, its core wire 68 and coat 61a are fixed to base 42 by resin 74. For this reason, signal lines 61 are firmly bonded to imaging apparatus 40. Therefore, even if an external force acts on signal lines 61 upon bending operation of insertion section 12 of the endoscope, they will not be disconnected from the imaging apparatus. Electrical parts associated with imaging apparatus 40 are mounted on coupling member 76 located outside bendable portion 20. No mounting space for electrical parts is required around imaging apparatus 40, and the distal end section of insertion section 12 can be made compact. A smaller number of parts are mounted around a arranged where coupling member 76 is arranged than that around the distal end portion of insertion portion 12, so that connecting operation and the like for the electrical parts can be facilitated.

Upon reduction in size of the imaging apparatus, the diameter and length of the distal end portion of the insertion portion of the endoscope can be decreased as in the first embodiment.

The present invention is not limited to the above embodiments, and various changes and modifications may be made within the spirit and scope of the invention. For example, the cover plate of the imaging apparatus is not limited to glass, but can be formed of a transparent resin.

What is claimed is:

1. A solid-state imaging apparatus comprising:
a base;
a solid-state imaging element chip mounted on the base and having a light-receiving section and a plurality of electrodes;
a plurality of leads provided at the base; and
a transparent cover fixed to the base to face the light-receiving section of the chip, the cover having a surface facing the light-receiving section and a lead pattern which is formed on the surface and electrically connects the leads and the electrodes.

2. An apparatus according to claim 1, which further comprises: a plurality of signal lines, each of said signal lines having a distal end portion connected to a corresponding one of the leads; and a coating member for covering the leads and the distal end portions of the signal lines.

3. An apparatus according to claim 1, wherein each of said leads has a cylindrical shape, and extends outwardly from the base.

4. An apparatus according to claim 3, wherein an extended end of each of said leads is obliquely cut.

5. An apparatus according to claim 3, which further comprises: a plurality of signal lines, each of the signal lines having a core wire which is inserted and fixed to the interior of the extended end of the lead.

6. An apparatus according to claim 3, which further comprises: a second lead pattern formed on the base end electrically connected to the extended ends of the leads; and an electrical part mounted on the base and electrically connected to the second lead pattern.

7. An endoscope comprising:
an operation section;
an insertion section extending from the operation section;
an objective optical system, arranged in a distal end portion of the insertion section, for imaging an optical image; and
a solid-state imaging apparatus, arranged in the distal end portion of the insertion section, for converting the optical image imaged by the objective optical system into an electrical signal and outputting the electrical signal, said imaging apparatus comprising: a base; a solid-state imaging element chip mounted on the base and having a light-receiving section and a plurality of electrodes; a plurality of leads provided at the base; and a transparent cover fixed to the base to face the light-receiving section of the chip, the cover having a surface facing the light-receiving section and a lead pattern which is formed on the surface and electrically connects the leads and the electrodes.

8. An endoscope according to claim 7, wherein said insertion section includes a flexible sheath extending from the operation section and a bendable portion provided at a distal end of the sheath, and a distal end member fixed to a distal end of the bendable portion, said solid-state imaging apparatus being attached to the distal end member, and which further comprises: a plurality of signal lines, each having a distal end portion connected to a corresponding one of the leads of the solid-state imaging apparatus and extending from the imaging apparatus toward the operation section.

9. An endoscope according to claim 8, wherein each of said leads extends from the base and has a cylindrical shape, and the distal end portion of each of the signal lines is inserted and fixed to an interior of an extended end of a corresponding one of the leads.

10. An endoscope according to claim 8, wherein said solid-state imaging apparatus has a coating member fixed to the base and covering the distal end portions of the signal lines and the leads.

11. An endoscope according to claim 8, which further comprises: a coupling member arranged in the sheath, and electrical parts fixed to the coupling member, and wherein each of said signal lines has a first portion extending from the solid-state imaging apparatus to the coupling member and a second portion extending from the coupling member toward the operation section, the first and second portions being coupled to each other at a position of the coupling member and being electrically connected to the electrical parts.

\* \* \* \* \*